(12) United States Patent  (10) Patent No.: US 7,819,119 B2
Ho  (45) Date of Patent: Oct. 26, 2010

(54) USER INTERFACE HAVING A PIVOTABLE COUPLING

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 332 days.

(21) Appl. No.: 11/243,379

(22) Filed: Oct. 4, 2005

(65) Prior Publication Data

US 2006/0076019 A1  Apr. 13, 2006

Related U.S. Application Data

(60) Provisional application No. 60/617,265, filed on Oct. 8, 2004.

(51) Int. Cl.
A62B 17/04 (2006.01)
A62B 9/04 (2006.01)
A62B 18/02 (2006.01)
A62B 18/08 (2006.01)
A62B 7/00 (2006.01)

(52) U.S. Cl. ............... 128/206.24; 128/201.22; 128/201.23; 128/202.27; 128/205.25; 128/206.12; 128/206.13; 128/206.18; 128/206.21; 128/206.23; 128/206.26; 128/206.27; 128/206.28; 128/207.11; 128/207.13; 128/207.18

(58) Field of Classification Search ............ 128/201.22, 128/201.23, 202.27, 205.25, 206.12, 206.13, 128/206.18, 206.21, 206.23, 206.24, 206.26, 128/206.27, 206.28, 207.11, 207.13, 207.18, 128/DIG. 26

See application file for complete search history.

(56) References Cited

U.S. PATENT DOCUMENTS

| 6,119,693 | A | 9/2000 | Kwok et al. |
| 6,412,487 | B1 | 7/2002 | Gunaratnam et al. |
| 6,467,483 | B1 | 10/2002 | Kopacko et al. |
| 7,044,130 | B2 * | 5/2006 | Jones et al. ............ 128/206.21 |
| 2003/0075180 | A1 | 4/2003 | Raje et al. |
| 2003/0221691 | A1 | 12/2003 | Biener et al. |
| 2004/0094159 | A1 | 5/2004 | Kwok et al. |
| 2004/0216746 | A1 | 11/2004 | Jones, Jr. et al. |
| 2005/0172969 | A1 * | 8/2005 | Ging et al. ............. 128/206.24 |

FOREIGN PATENT DOCUMENTS

WO  WO 02/11804 A2  2/2002

OTHER PUBLICATIONS

PCT International Search Report, International Appl. No. PCT/US05/35856, Feb. 21, 2008.

* cited by examiner

*Primary Examiner*—Patricia M Bianco
*Assistant Examiner*—Nihir Patel
(74) *Attorney, Agent, or Firm*—Michael W. Haas

(57) ABSTRACT

A patient interface having a cushion for engagement with the face of a user, a shell having an extension with a forehead support connected to the extension. The forehead support has a hinge so that the forehead support can be deformed to conform to the user's forehead. The patient interface also has a pivotable coupling defined by a body and a coplanar conduit that extends radially from the body. The coupling also has a port that allows access within the cavity formed by the cushion so that the port and coupling may rotate together.

18 Claims, 9 Drawing Sheets

USER INTERFACE HAVING A PIVOTABLE COUPLING

CROSS-REFERENCE TO RELATED APPLICATIONS

Under the provisions of 35 U.S.C. §119(e), this application claims the benefit of U.S. Provisional Application Ser. No. 60/617,265, filed Oct. 8, 2004.

BACKGROUND OF THE INVENTION

1. Field of the Invention

The present invention pertains to user interfaces, and, in particular, to self-conforming, compact user interfaces that have a pivot coupling with a port so that both the coupling and port rotate together.

2. Description of the Related Art

A variety of delivery systems are known that provide gas at positive pressure for consumption by a patient. The uses and applications of such systems vary. Some such systems have been developed for the treatment of sleep apnea and other sleep related disorders.

Sleep apnea syndrome results in episodic upper airway obstruction during sleep. As a consequence, there is repeated interruption of sleep in the patient. Positive airway pressure (PAP) devices have been developed to treat this disorder. A typical PAP device comprises a flow generator (e.g., a blower) that delivers gas via a delivery conduit to a user interface, such as a mask. It is also known to deliver the PAP as a continuous positive airway pressure (CPAP), a variable airway pressure, such as a bi-level pressure that varies with the patient's respiratory cycle (Bi-PAP), or an auto-titrating pressure that varies with the monitored condition of the patient. Pressure support therapies are also provided to treat other medical and respiratory disorders, such as Cheynes-Stokes respiration, congestive heart failure, and stroke.

Much development has revolved around user interfaces. In order to be effective, a user interface must be both comfortable and provide an adequate seal. If the user interface is not comfortable, patient compliance will be low. Yet, if the user interface does not provide an adequate seal, the gas will not be appropriately delivered to the user. Often patients use these devices while they are asleep. It is not uncommon for the user to be restless or move around. In this application, the goal of providing a user interface that is comfortable is at odds with the goal of maintaining a seal.

One device exemplary of the state of the art is disclosed in U.S. Patent Application No. US-2003-0075180 ("the '180 application"). The user interface disclosed in this application has a rigid shell that supports a cushion and a fixed coupling with a coupling conduit. The coupling conduit extends generally upwardly from the shell along the bridge of the user's nose towards the user's forehead and includes a ball-and-socket joint to provide the coupling conduit with a limited range of motion. As the user moves their head, the ball-and-socket joint will pivot so that the user interface will remain properly sealed to the face of the user. The coupling conduit is attached to a gas delivery conduit which, in turn, is connected to a ventilator to apply positive pressure. Returning to the patient interface, the shell is connected to the cushion by a retaining clip. The retaining clip fits into a channel formed on the shell. A corresponding retaining lip extends about the periphery of the cushion thereby defining the channel about the periphery of the cushion. The retaining clip engages the channel about the cushion. In other words, the retaining clip and the retaining lip on the cushion interlock in a c-shaped cross-section. A plurality of integral detents formed on the retaining clip fit through slots in the shell and hold the retaining clip in place. To secure the user interface in place to the user, the shell includes an extension portion that extends upward from the mask towards the user's forehead. The extension portion is connected to a flexible horizontal strap that engages the sides and the rear rather than the front of the user's head so that the flexible horizontal strap is spaced from the user's forehead to reduce pressure in this region.

Although the device disclosed in the '180 application is adequate for its intended purpose, it also has several drawbacks as well. Even though the ball-and-socket joint provides some range of motion, it is limited such that the coupling conduit must still be generally directed upward in the direction of the user's forehead. This device is ineffective at redirecting the coupling conduit in any other general direction. Since users often use these interfaces while they are asleep, it would be desirable to have a maximum degree of freedom so that the user can freely move their head, or even turn over in bed, without affecting the seal between the user interface and the user.

Another drawback to this device is that it secures the patient interface with a flexible horizontal strap that contacts the sides of the user's head rather than the user's forehead. Although presented as an advantage, patients often wear these user interfaces while they are asleep. Many such users sleep on their side for at least a portion of the night. When pressure from a pillow or bed is applied to the side of the user's head, the flexibility of this design combined with the lack of forehead support will allow the user interface to shift on the user's face and may become uncomfortable or break the seal between the user interface and the user compromising both comfort and the seal.

This device has yet another drawback. The cushion is secured to the mask with a retaining clip that engages the retaining lip of the shell in a c-shaped interlocking configuration. However, if a tensile force is applied to the shell on one end and the cushion on the other, the cushion is likely to pull free of the retaining clip thus requiring reattachment. Because user interfaces experience a great deal of abuse when used, it is undesirable to have a cushion that can be easily pulled free of the shell. In addition, this device does not disclose a pressure port to monitor the internal pressure within the patient interface.

Other patient interfaces have been suggested to advance the art. For instance the device described in U.S. Pat. No. 6,467,483 ("the '483 patent") discloses a patient interface that has a shell attached between a flexible cushion and a coupling conduit. The shell includes a shell body and a rigid support that supports a forehead pad. Together, the cushion and rigid support hold the user interface on the face of the user. The distance between the rigid support and the shell body may be adjusted to accommodate the unique facial characteristics of different users. Another feature of note is that in this device the coupling conduit is a rotatable elbow that provides 360 degrees of rotation thereby allowing the gas delivery conduit to be directed in a multitude of directions from the patient interface rather than being limited to any one direction. Further unlike the device disclosed in the '180 application, the shell of this user interface has a port for the attachment of a variety of items when access to the interior of the user interface is desired such as a pressure port.

Although the device described in the '483 patent has advanced the art, it can still be further improved upon. Because the coupling conduit is free to rotate 360 degrees, it may become tangled with the port that extends from a fixed location on the shell. If the user repeatedly spins the coupling conduit, each rotation may further tangle the coupling conduit with whatever is connected to the port. In addition, the forehead pad is supported by a rigid support. Even though the distance between the rigid support and the shell body may be adjusted, this may still not be comfortable for some users. Some users may have facial characteristics that are not precisely suited to the contours of this rigid extension. In this circumstance, the patient interface may not fit properly or may simply be uncomfortable.

Another drawback to the device disclosed in the '483 patent is that the coupling conduit is an elbow-type connector that extends a substantial distance away from the shell body. This coupling conduit may be more likely to become tangled with other items in the user's environment. In addition, many users of patient interface devices are self-conscious about wearing the device and would prefer a compact, low-profile user interface. Having a coupling conduit that extends a substantial distance away from the shell body is likely to be deemed undesirable by many users.

Accordingly, it would be desirable to have a patient interface that reduces the likelihood that the pressure port and gas delivery conduit will become tangled during use. It would also be desirable to have a patient interface that can be securely mounted to multiple different users. Further, it would be desirable to have a patient interface that is easy to assemble but also reduces the possibility of the cushion becoming disconnected from the shell during use.

SUMMARY OF THE INVENTION

In accordance with the broad teachings of the invention, a patient interface is disclosed which is configured to deliver gas to a user. The patient interface includes a cushion, a shell and a coupling that are connected together. The cushion has a cavity, and the shell has an opening that is connected to the coupling, which in turn, is connected to a gas delivery conduit such that a breathing gas may be conveyed to the user through the cavity and the opening. In one aspect of the invention, the coupling is pivotable and has a port such that the port and the coupling rotate together. In another aspect of the present invention, the user interface includes a retention ring that has detents which pass through slots in the cushion to prevent the cushion from being pulled free from the shell. In still another aspect of the present invention, the user interface includes a forehead support that has a hinge so that the forehead support may flex to conform to a particular user's forehead.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
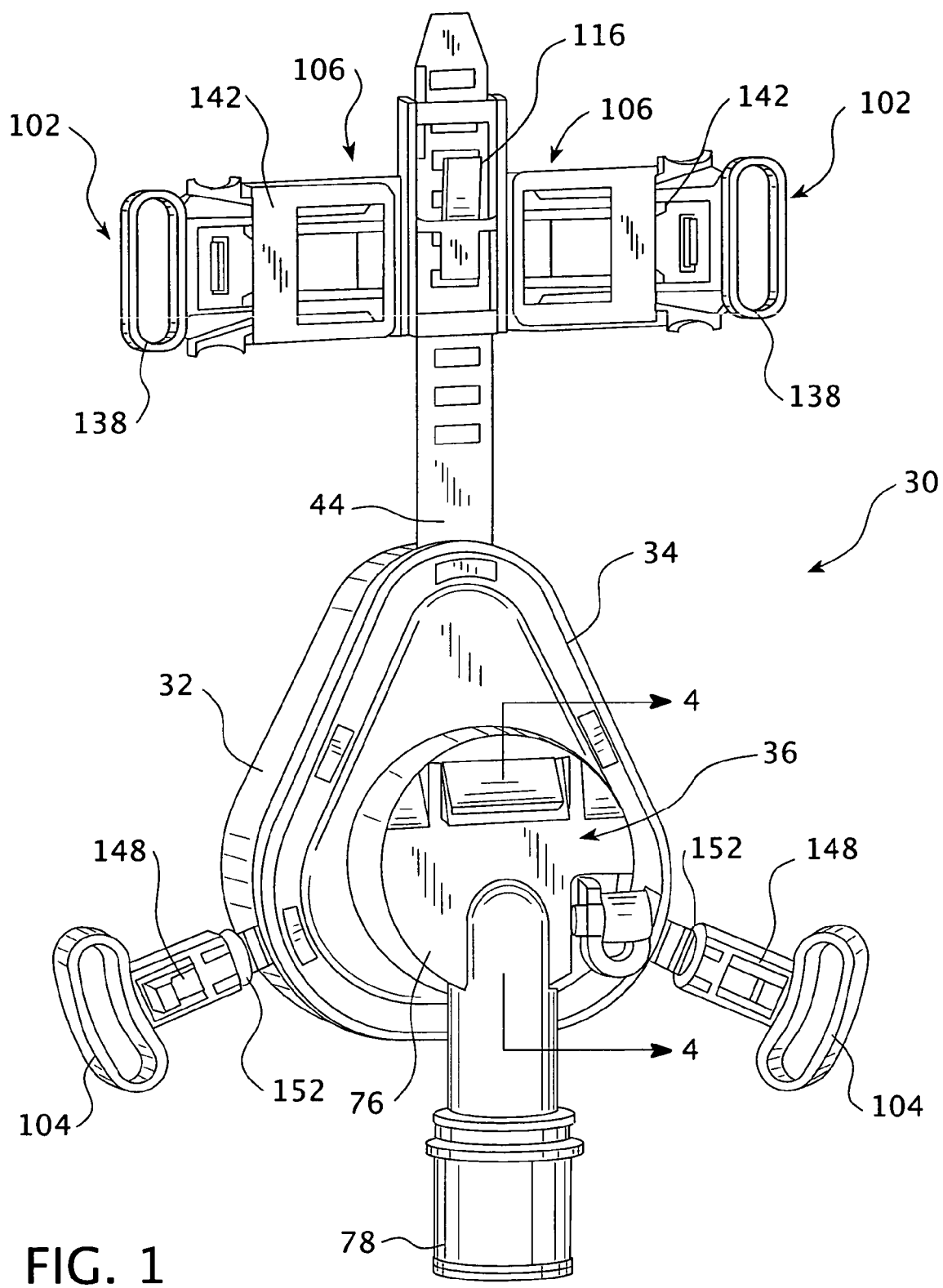
FIG. 1 is a front perspective view of a user interface according to the principles of the present invention.
Figure 2:
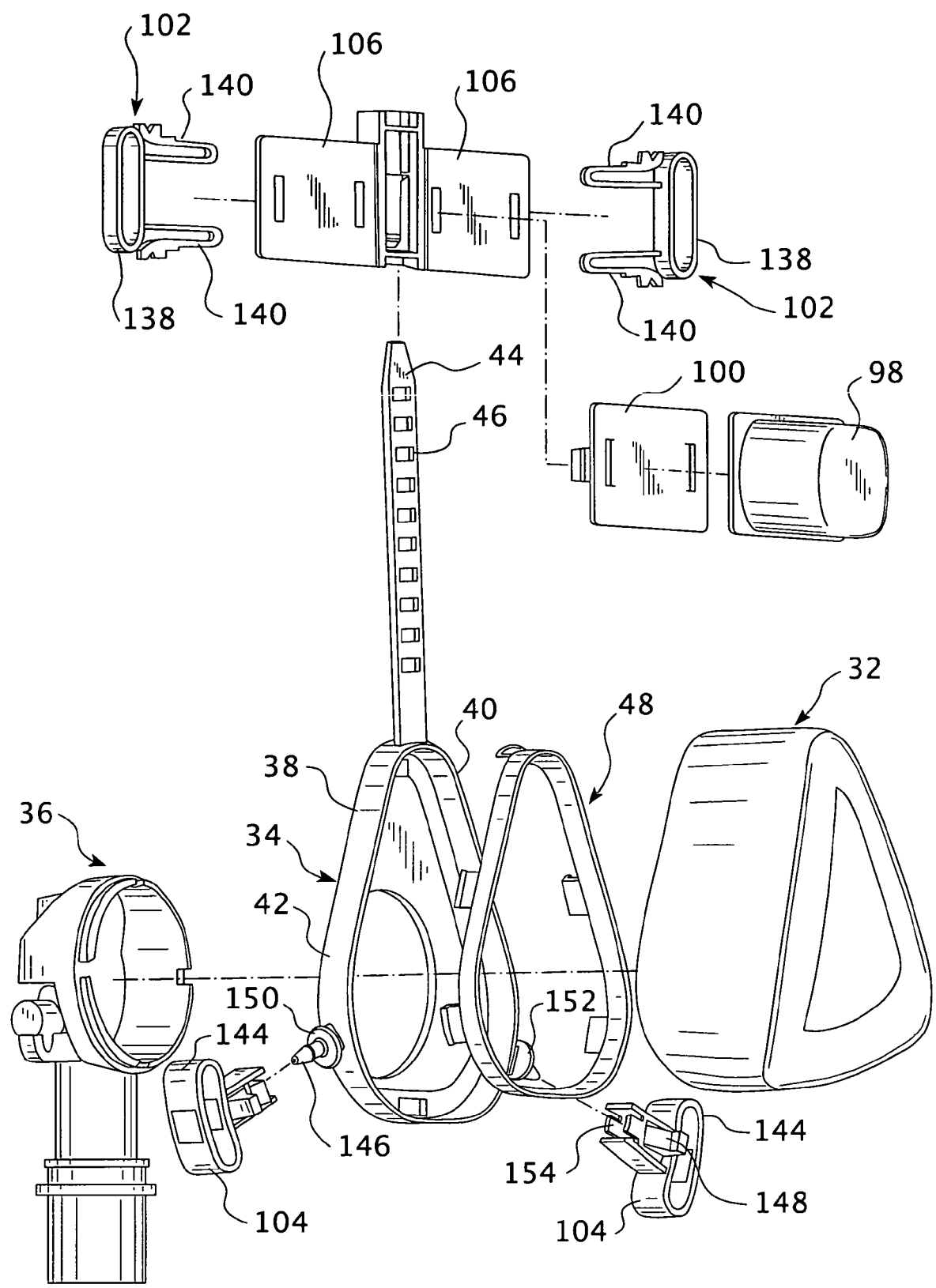
FIG. 2 is an exploded rear perspective view of the user interface.

FIG. 1 schematically illustrates an exemplary embodiment of a user interface 30 according to the principles of the present invention. Generally, the user interface has a cushion 32 connected to a shell 34, which in turn, is connected to a coupling 36. The user interface is typically connected to a gas delivery conduit, not shown, to provide a breathing gas to the user. Of course, the present invention could be used in other configurations including both positive and negative pressure systems. Turning to FIG. 2, shell 34 has an outer surface 38 and an inner surface 40. Extending about the inner surface is a skirt 42 which extends over a portion of the cushion to provide hoop strength to the shell. The shell also includes an extension 44 which has a plurality of catches 46, explained in further detail below. The extension is formed from a flexible material such that it may self-adjust to the unique facial characteristics of various users.

Figure 3A:
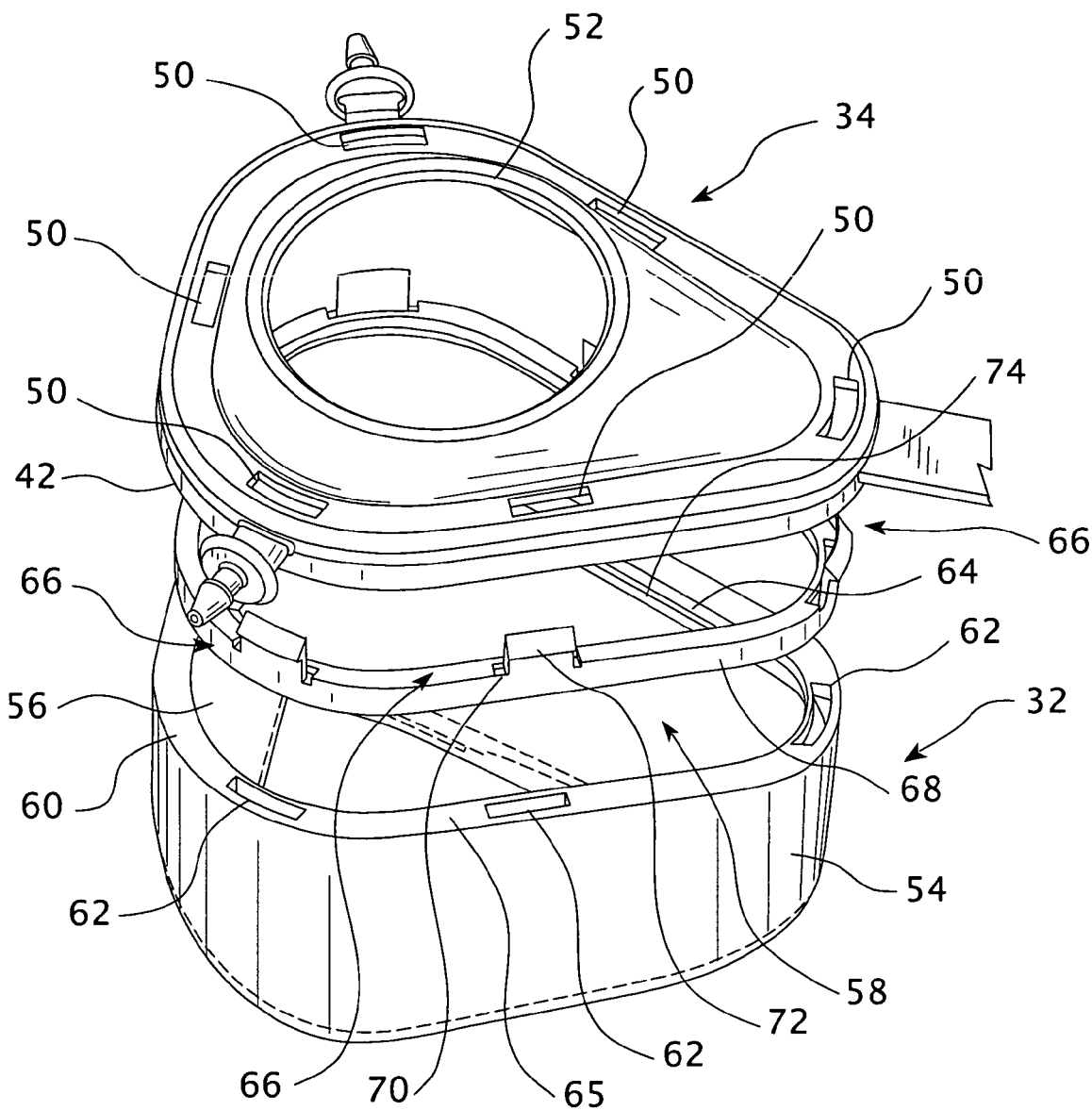
FIG. 3A is an exploded front perspective view of a shell, retaining ring, and cushion of the user interface.

User interface 30 also includes a retaining ring 48 which interconnects cushion 32 with shell 34. Mechanically interconnecting the shell and the cushion can be performed with greater reliability in an industrial manufacturing environment than interconnecting the shell and cushion with an adhesive. As best appreciated with reference to FIG. 3A, shell 34 has slots 50 formed about an opening 52. Cushion 32 is configured to be attached to the shell and provide a flexible seal with the user. As shown in FIG. 3A, cushion 32 has a generally triangular shape. However, various other shapes may be used without departing from the spirit and scope of the invention.

Figure 3B:
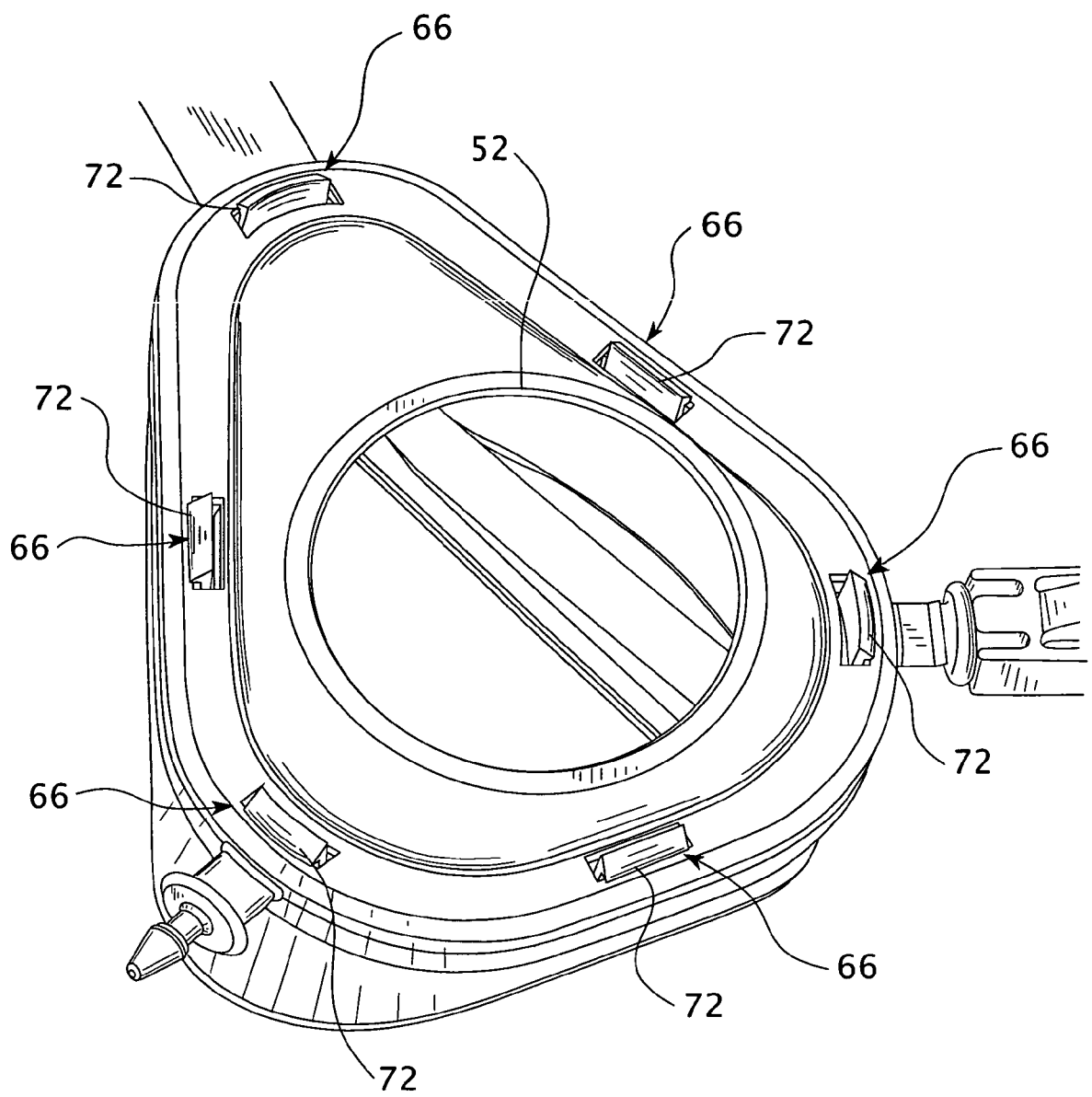
FIG. 3B is a front perspective view of the assembled shell, retaining ring, and cushion of FIG. 3A.

Cushion 32 has an outer wall 54 and an inner wall 56. Inner wall 56 defines a cavity 58 into which the user will place their nose when user interface 30 is in use. Cushion 32 has a lip 60 with slots 62. Extending from the lip is a flange 64 that defines an opening 65. Retaining ring 48 has detents 66 extending from ring body 68. Each detent 66 is defined by a projecting portion 70 and a hook portion 72. Detents 66 are configured to pass through slots 62. As seen in FIG. 3B, detents 66 engage a portion of outer surface 38 of shell 34 and capture cushion 32 between shell 34 and retaining ring 48 to secure cushion 32 in place.

Figure 4:
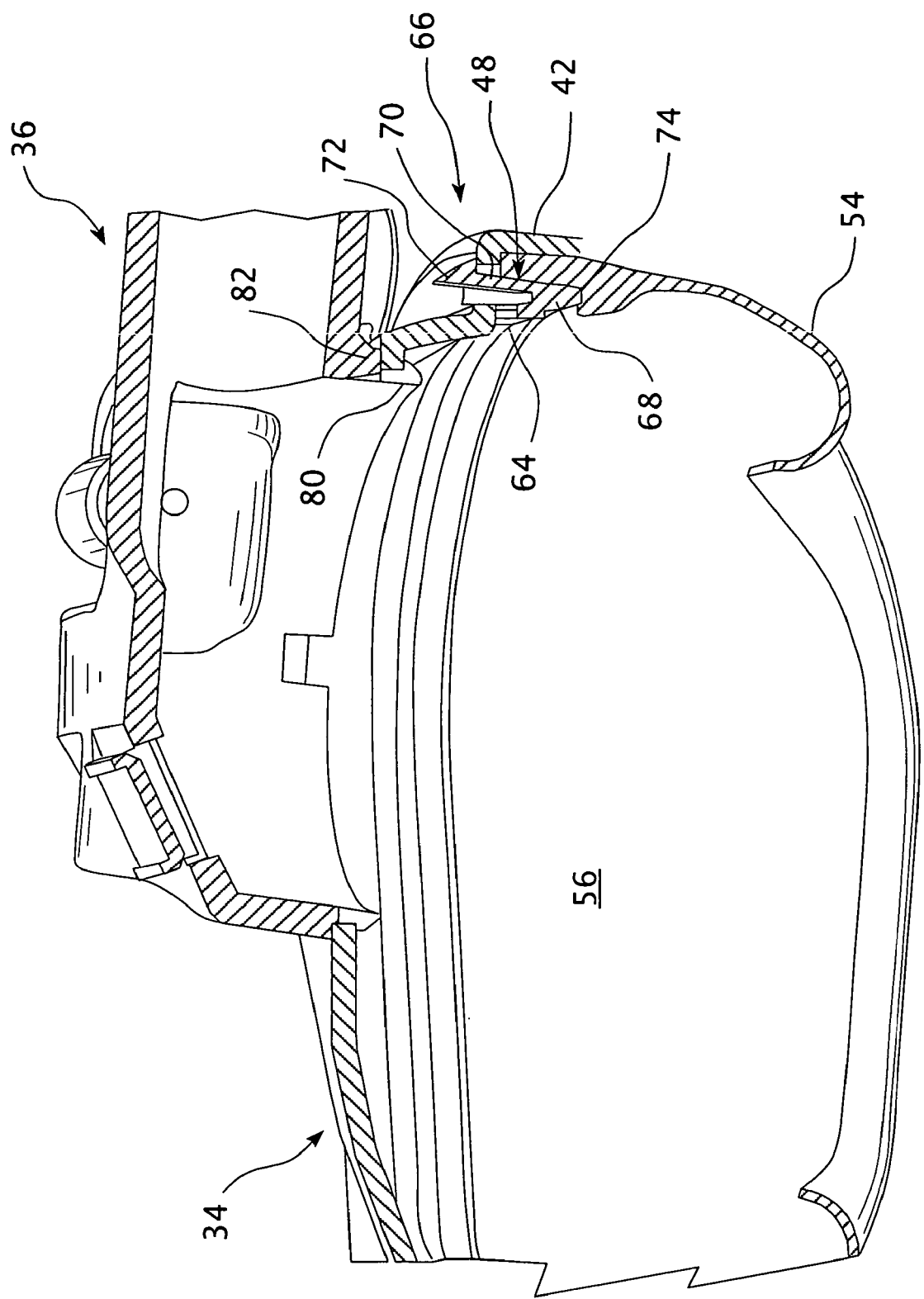
FIG. 4 is a cross-sectional view of the assembled shell along line 4-4 of FIG. 1.

With reference to FIG. 4, cushion 32 has a ledge 74 which extends about inner wall 56 of the cushion adjacent lip 60. Ring body 68 is captured between lip 60 and ledge 74. One unique feature of the present invention is the interconnection of cushion 32 with shell 34. Unlike prior art devices in which the cushion can be disconnected from the shell by applying a tensile force between the cushion and the shell, the present invention reduces the possibility that cushion 32 will become disconnected from shell 34 during use. This result is achieved by passing detents 66 through slots 62 in the cushion 32 and through slots 50 in shell 34 to anchor cushion 32 in place. In order to remove cushion 32, the user needs to disengage detents 66 thus preventing the possibility of inadvertent removal.

Figure 5A:
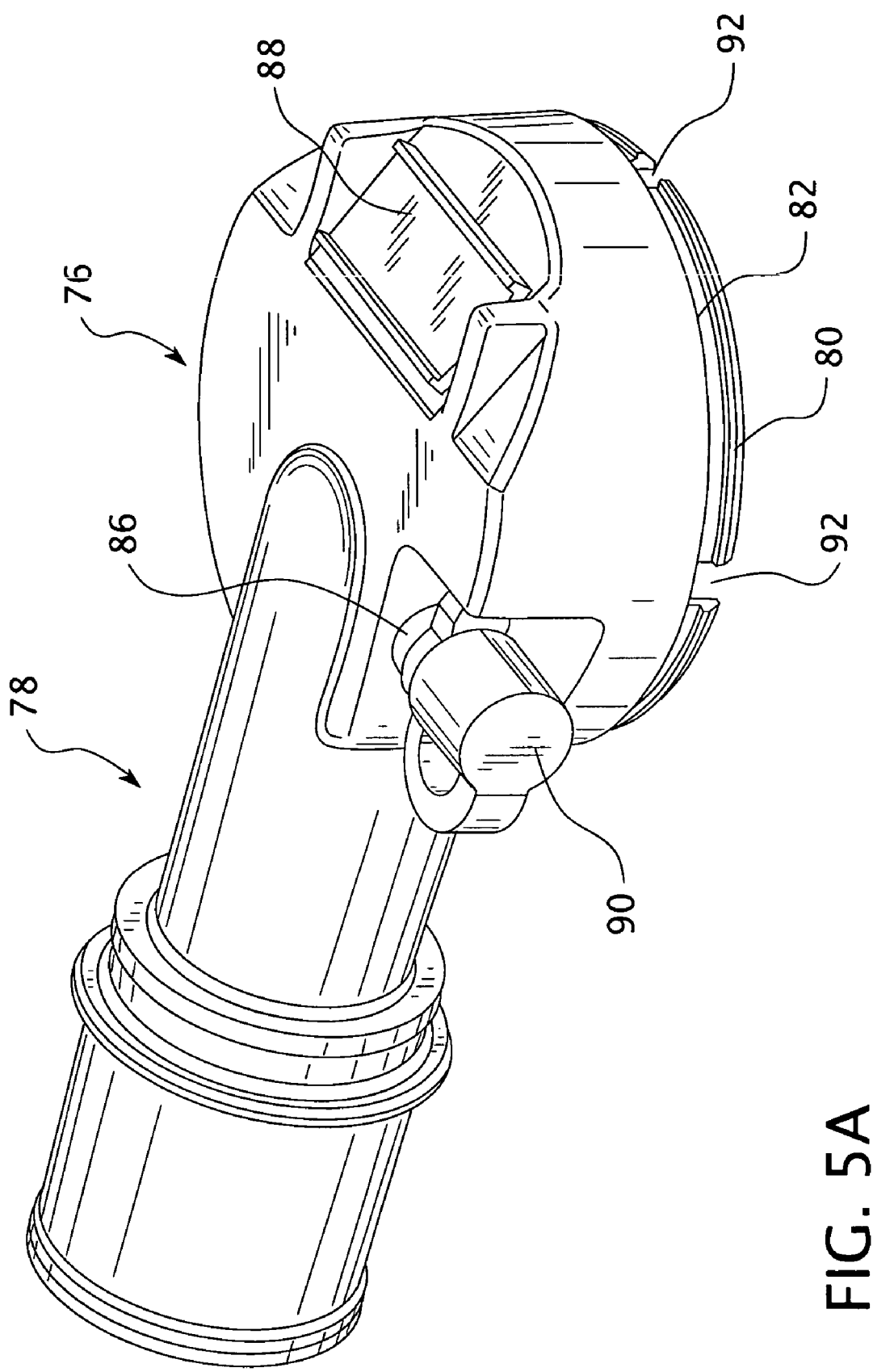
FIG. 5A is a front perspective view of a coupling.

Another aspect of the present invention pertains to coupling 36. As seen in FIG. 5A coupling 36 has a coupling body 76 and a coupling conduit 78 which interconnects coupling body 76 with the gas delivery conduit, not shown. Rather than using a contemporary elbow connector, the present invention provides a coupling that extends a minimum distance away from the user. In order to reduce the overall distance that coupling 36 extends from a user's face, coupling body 76 and coupling conduit 78 are coplanar. Coupling body 76 is preferably cylindrical with coupling conduit 78 extending radially outward from the coupling body. Of course, the coupling could have a variety of other shapes without departing from the present invention.

Coupling body 76 has a bead 80 and a shoulder 82 extending around opening 84. Returning to FIG. 4, one can best appreciate that bead 80 is passed through opening 52 on shell 34 such that shell 34 is captured between bead 80 and shoulder 82. This configuration allows for coupling body 76 to be rotated while remaining engaged with shell 34. Coupling 36 also has an exhaust port 88. Exhaust port 88 may include a one-way valve, not shown, such as a flapper valve or duck bill valve.

As seen in FIG. 5A, coupling 36 also has a port 86. Port 86 may be used for any function in which it is desirable to access cavity 58 within cushion 32. One such use for port 86 is as a connection location for a pressure sensor, not shown, via a tube, not shown. Of course, a variety of other devices may be attached to port 86 of coupling body 76 without departing from the spirit and scope of this invention such as electrical wires or tubes used to monitor a variety of features. Port 86 can also be used as an access location for delivering items to the user other than the breathing gas. Since port 86 and coupling conduit 78 are both on coupling 36, the port and coupling conduit will rotate together thus preventing them from becoming tangled. Another significant feature of the present invention is that the coupling body 76 may rotate a full 360 degrees so that the user can pivot the coupling to any angle that is the least intrusive. Patient interfaces are often used during sleep. Users of the present invention are free to switch sides or move their head while they are asleep without compromising the seal between the users' face and cushion 36 by simply rotating coupling 36 to a convenient location. When port 86 is not in use, the user may seal it with cap 90.

Figure 5B:
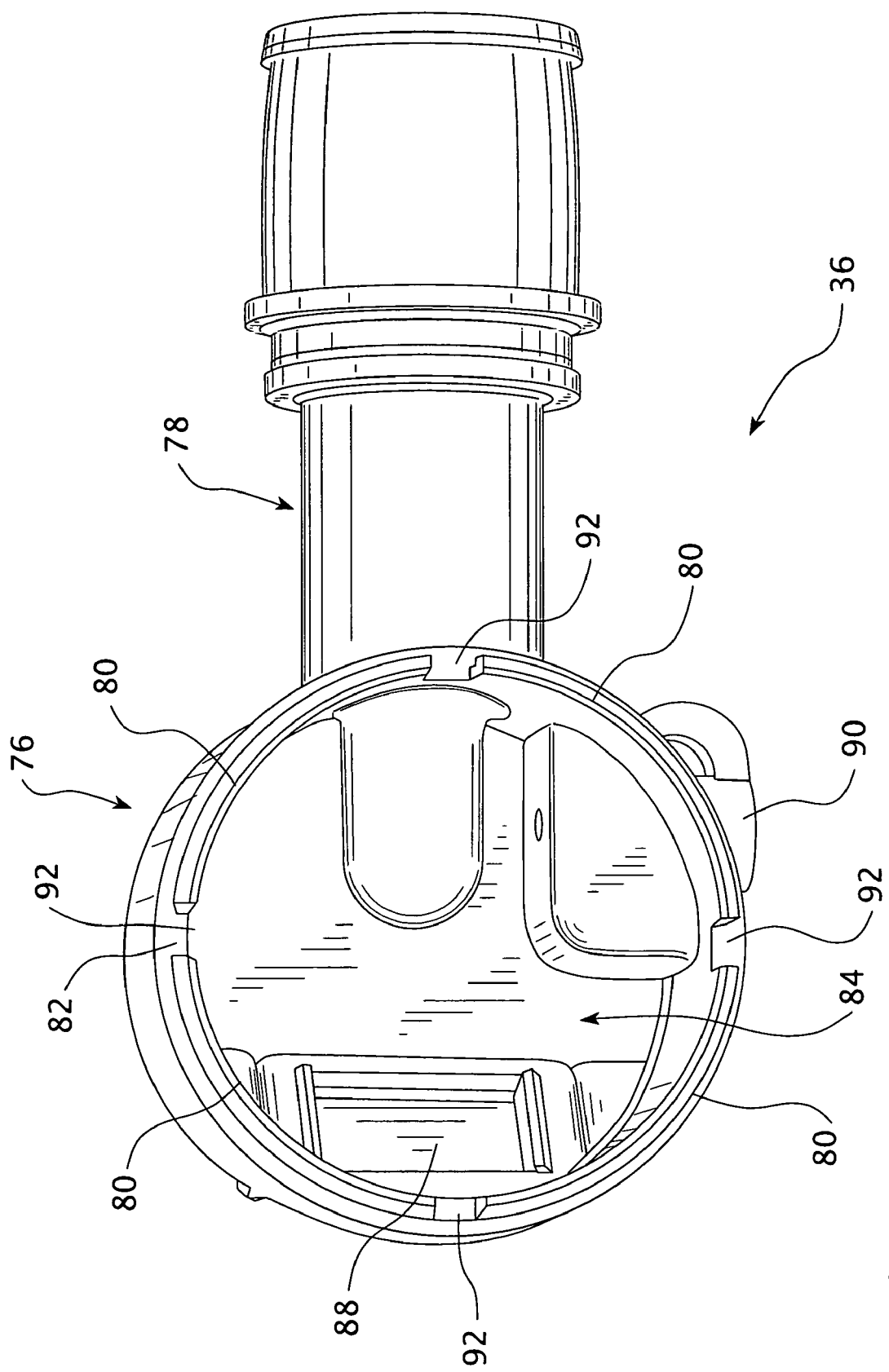
FIG. 5B is a rear perspective view of the coupling.

Turning to FIG. 5B, bead 80 may be discontinuous about coupling body 76. For instance, bead 80 may be interrupted by grooves 92. Grooves 92 reduce the hoop strength of coupling 36 in the region about bead 80 thus allowing bead 80 the ability to elastically flex inward as it is pressed into place in opening 52. Interconnecting the coupling with the shell is accomplished by pressing coupling body 76 on to outer surface 38 of shell 34. As the coupling body and shell are pressed together, the bead 80 will flex inward and then spring back once bead 80 is passed through opening 52 thus capturing bead 80 such that it provides a bearing surface with inner surface 40 of shell 34 in the region about opening 52.

Figure 6:
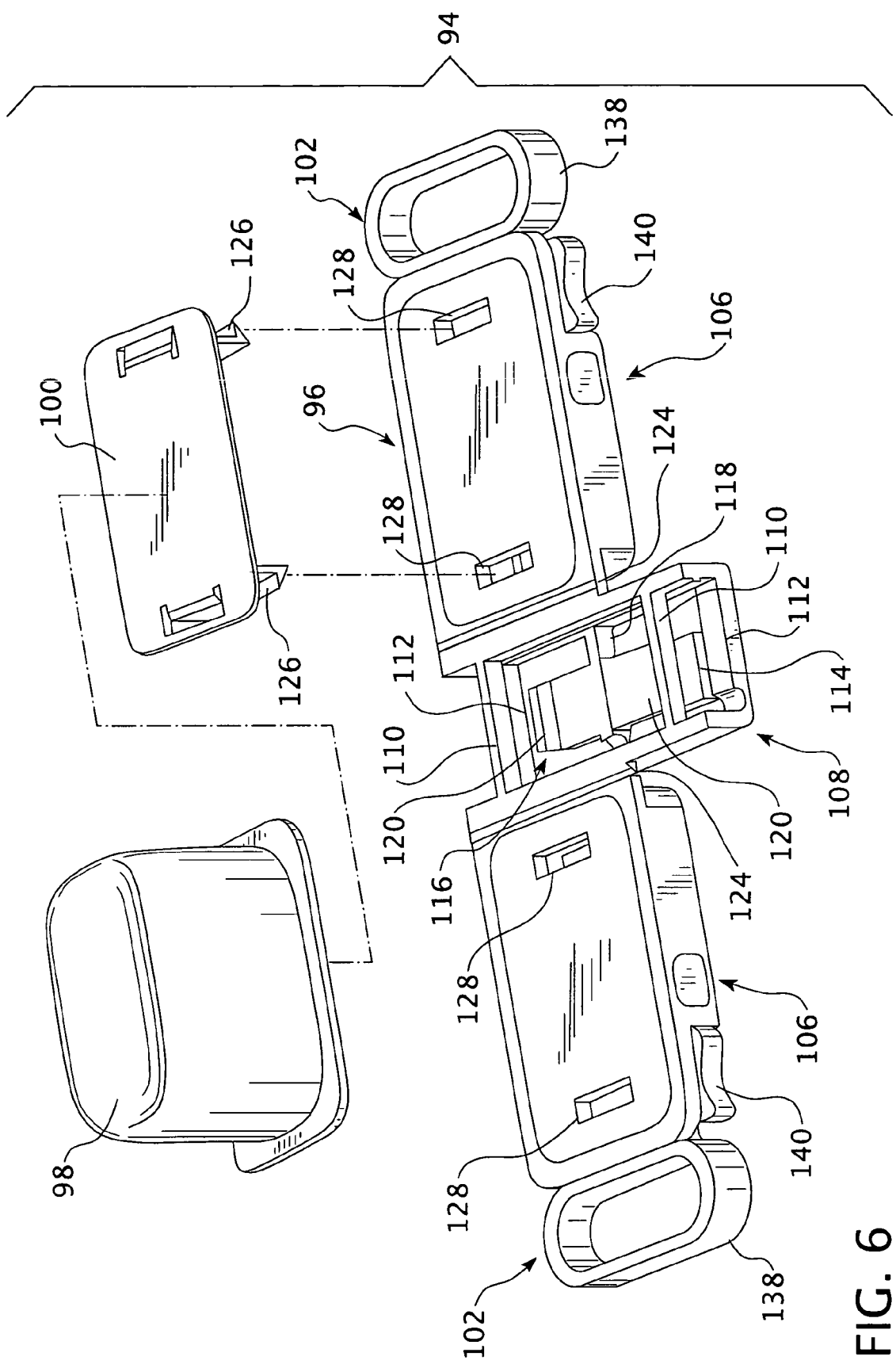
FIG. 6 exploded perspective view of the forehead support of the user interface.

With reference to FIGS. 1 and 6, patient user interface 30 of the present invention also includes a forehead support 94. Forehead support 94 disperses the forces otherwise concentrated in the junction between the user and the cushion. In addition, the forehead support provides additional support to the device to prevent the user interface from being inadvertently repositioned and potentially undermine the seal between the cushion and the user.

The user interface has an adjustable mount 96 and pads 98 supported by backing plates 100. Adjustable mount 96 has removable forehead latches 102. Similarly, shell 34 also includes removable shell latches 104. Adjustable mount 96 has wings 106 connected by a central fastener portion 108.

The fastener portion has a first set of ribs 110 and a second set of ribs 112 defining a passageway 114 therebetween. Fastener portion 108 also includes a pawl 116. Pawl 116 is defined by a torsion spring 118 connected to an elongate body 120 and a tooth 122. Tooth 122 is sized to engage catches 46 on extension 44 so that the distance between forehead support 94 and shell 34 may be adjusted to suit a particular user. When the user desires to adjust the forehead support, the user presses the elongate body 120 to rotate torsion spring 118 until tooth 122 disengages a particular catch. The user may then slide the forehead support to an appropriate distance from shell 34 and release elongate body 120 such that tooth 122 reengages with a different catch.

Figure 7:
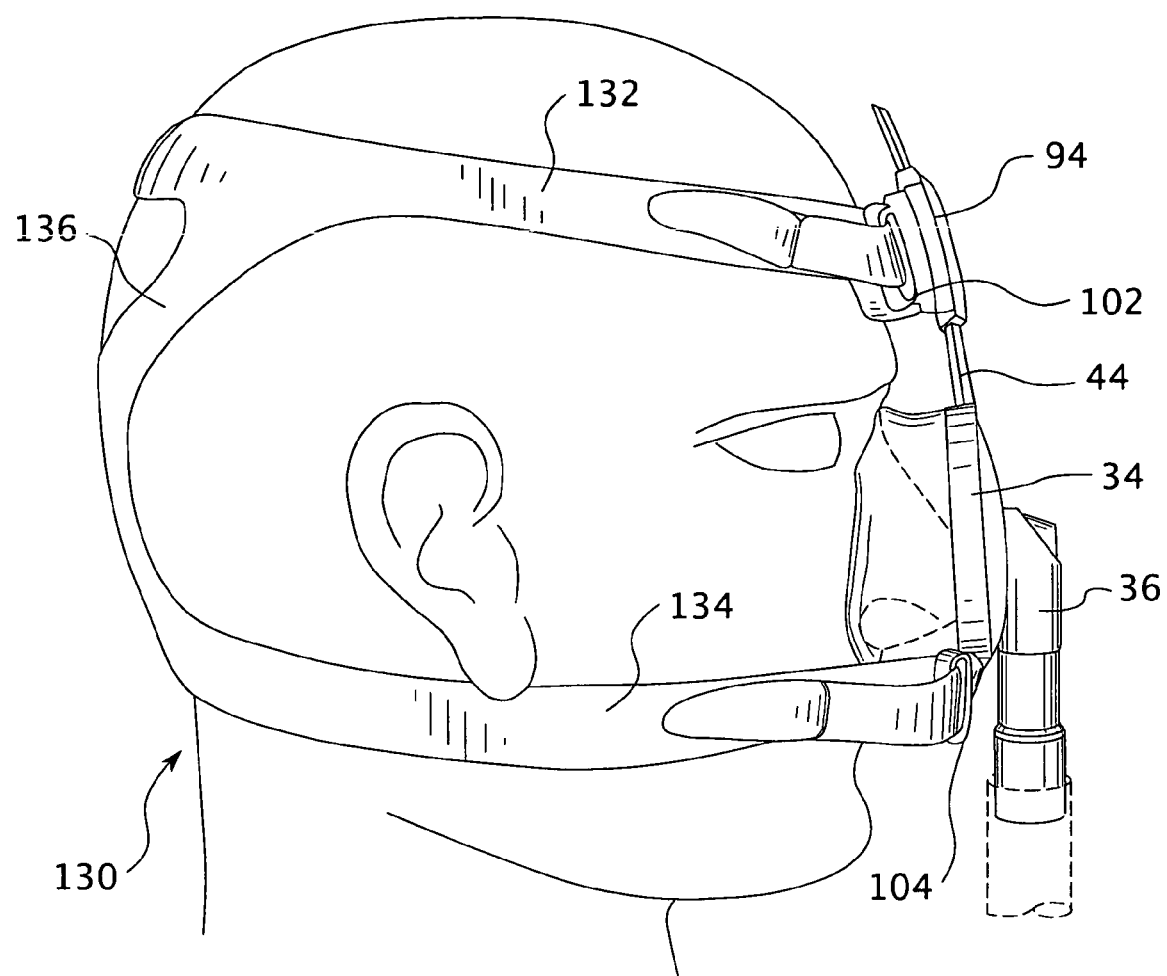
FIG. 7 is a side elevational view of the user interface on a user's face.

Another unique aspect of the present invention is that adjustable mount 96 also has hinges 124. As seen in FIG. 7, hinges 124 permit forehead support 94 to flex such that it may better conform to a particular user's head. In combination with the flexibility of extension 44, the flexibility of forehead support 94 provides two planes of flexibility both transversely across the user's forehead and longitudinally along the bridge of the user's nose. Preferably, hinges 124 and pawl 116 are formed integrally with adjustable mount 96. However, hinges 124 and pawl 116 could be a separate discrete part without departing from the teachings of this invention. Pads 98 are attached to backing plates 100 with an adhesive. Backing plates 100 are, in turn, connected to adjustable mount 96 with legs 126 which engage apertures 128. Of course, any other contemporary method of attaching pads 98 to adjustable mount 96 may be used as well.

The present invention may be assembled easily in a manufacturing environment. Preferably, this is achieved through use of multiple integral features that are incorporated into a common structure. To assemble the user interface, the retaining ring is placed within cushion 32 with detents 66 extend out slots 62. Next, shell 34 is pressed together with retaining ring 48 so that detents 66 pass through slots 50 and spring into engagement with outer surface 38 of shell 34. Coupling 36 is pressed into engagement with opening 52 of shell 34. Forehead support 94 is assembled by adhering pads 100 to backing plates 100. Backing plates 100 are coupled to adjustable mount 96 by engaging legs 126 with apertures 128. Extension 44 is feed between upper ribs 110 and lower ribs 112 until pawl 116 engages the appropriate catch 46.

To use the present invention, the user will connect a headgear assembly 130, as seen in FIG. 7, to latches 102 104. In particular, the headgear assembly 130 includes forehead straps 132 connected to forehead latches 102 and shell straps 134 connected to shell latches 104. To provide additional support forehead straps and shell straps are interconnected by web 136. Of course, any contemporary headgear assembly 130 may be used in accordance with the present invention.

Latches 102 and 104 provide a unique mechanism for interconnecting headgear 130 and shell 34. Returning briefly to FIGS. 1 and 2, latches 102 include buckles 138 having cantilevered arms 140. The cantilever arms are captured by sockets 142 formed on wings 106. The cantilevered arms may be disconnected from the sockets by squeezing the cantilever arms on each buckle 138 together so that the user may easily remove or adjust the forehead latches. Similarly latches 104 have a two-part construction with a buckle 144 releaseably attached to post 146. Buckle 144 has an opening 154 into which post 146 may be inserted. Buckle 144 also has a pair of integral pawls 148 adapted to engage an undercut 150 formed on post 146 to capture post 146 while still permitting post 146 to pivot relative to the shell. Post 146 includes a stop surface 152 to prevent over insertion of post 146 into buckle 144. Not only does this construction provide for adjustability, but it also permits the buckle to pivot relative to the shell to passively adjust to the particular facial characteristics of the user.

Collectively, the unique features of the present invention provide a compact user interface which self-adjusts to the user's facial characteristics. As seen in FIG. 7, coupling conduit is far more compact than prior art devices which use an elbow coupling. Since coupling 36 includes port 86, it reduces the potential for the gas delivery conduit to become tangled with items connected to port 86. Finally, extension 44 is formed from a flexible material and forehead support 94 includes hinges 124 so that the forehead support can flex. Together, these two features allow the user interface 30 to flex in two separate planes: one about the user's forehead and one about the user's nose. This flexibility of user interface 30 enhances the comfort of the device and permits use by multiple users with different facial characteristics.

While the present invention has been described as having a cushion that encapsulates the nasal region, it is to be understood that the present invention contemplates using other types of devices in conjunction with support body 36. For example, larger cushions that encapsulate the nose and mouth can be attached to the support body. Conversely, smaller cushions, or nasal prongs, that seal in or near the nares can be supported by the support body. In short, any interface suitable for sealing against the user can be used in the mask assembly of the present invention.

It should also be understood that the present invention is not intended to be limited to a particular material for cushion 32 or pads 98. For example, these components can be formed from a silicone, plastic, rubber, foam, gel, or any other material or combination of materials that provides a sufficiently comfortable interface with the user's skin. In addition, shell 34, coupling 36, retaining ring 48, and adjustable mount 96 can be formed from polypropylene, polyethylene or any other material which is sufficiently rigid to impart the necessary stability to patient interface 30 and sufficiently elastic so that the detents 66 and bead 80 will spring back into place.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface for use with a patient, the patient interface comprising:
    a cushion having a cavity;
    a shell having an opening in communication with the cavity, the shell having an extension extending from the shell; and
    a forehead support connected to the extension, the forehead support engaging a forehead of the patient, the forehead support having at least one hinge so that the forehead support may be deformed,
    wherein the at least one hinge is constructed and arranged such that deformation of the forehead support via the at least one hinge causes a shape of the forehead support to conform to a shape of the patient's forehead,
    wherein the forehead support is slidably connected to the extension for sliding movement of the forehead support relative to the extension and shell toward and away from the shell into a plurality of forehead support positions, and
    wherein the patient interface further comprises a forehead support lock that selectively locks the forehead support in a selected one of the plurality of forehead support positions.

2. The patient interface as recited in claim 1, wherein the forehead support comprises a plurality of pads.

3. The patient interface as recited in claim 1, wherein the at least one hinge is a plurality of hinges, wherein a pivotal axis of one of said plurality of hinges is spaced apart from a pivotal axis of another of said plurality of hinges.

4. The patient interface as recited in claim 1, wherein the at least one hinge is a living hinge.

5. The patient interface as recited in claim 1, wherein the extension is formed from a flexible material.

6. The patient interface of claim 1, wherein pivotal movement of the at least one hinge changes a shape of the forehead support.

7. The patient interface of claim 6, wherein the at least one hinge is constructed and arranged such that deformation of the forehead support via the at least one hinge flexes the forehead support along a plane of flexibility that extends transversely across the patient's forehead.

8. The patient interface of claim 7, wherein the extension is formed from a flexible material whose flexibility permits the forehead support to move relative to the shell along a plane of flexibility that extends along a bridge of the patient's nose.

9. The patient interface of claim 1, wherein the at least one hinge has a pivotal axis that is parallel to a direction that the extension extends away from the shell.

10. The patient interface of claim 1, wherein the at least one hinge has a pivotal axis that extends upwardly relative to a patient's forehead when the interface is worn by a patient.

11. The patient interface of claim 1, wherein the at least one hinge pivotally connects a lateral portion of the forehead support to a remainder of the forehead support.

12. The patient interface of claim 11, wherein the at least one hinge enables the lateral portion of the forehead support to move toward a patient's forehead relative to a remainder of the forehead support and engage the patient's forehead.

13. The patient interface of claim 1, wherein the at least one hinge pivotally connects two portions of the forehead support for relative movement therebetween.

14. A patient interface device for use with a patient, the patient interface device comprising:
    a shell;
    a forehead support connected to the shell, the forehead support configured to engage a forehead of the patient;
    a headgear assembly;
    at least one forehead latch interconnected between the headgear assembly and the forehead support, the forehead latch being releaseably coupled to the forehead support; and
    at least one shell latch interconnected between the headgear assembly and the shell, the shell latch being releasably coupled to the shell,
    wherein the at least one forehead latch is releaseably coupled to the forehead support via the at least one forehead latch such that release of the at least one forehead latch disconnects the forehead support from the headgear assembly.

15. The patient interface of claim 14, wherein the at least one forehead latch is constructed and positioned to uncouple the forehead support from the headgear assembly while the forehead support remains connected to the shell.

16. The patient interface of claim 14, wherein the forehead latch comprises first and second releasably connectable parts, the first part being connected to the forehead support, the second part being adjustably connected to the headgear assembly such that the at least one forehead latch may be disconnected without modifying a headgear assembly length setting.

17. The patient interface of claim 14, wherein the forehead latch is releasable from the forehead support without losing an adjustment position of the headgear assembly.

18. A patient interface device for use with a patient, the patient interface device comprising:
   a shell;
   a forehead support connected to the shell, the forehead support configured to engage a forehead of the patient;
   a headgear assembly;
   at least one forehead latch interconnected between the headgear assembly and the forehead support, the forehead latch being releaseably coupled to the forehead support; and
   at least one shell latch interconnected between the headgear assembly and the shell, the shell latch being releasably coupled to the shell,
   wherein the shell latch is pivotable relative to the shell.

* * * * *